(12) United States Patent
Han et al.

(10) Patent No.: US 11,806,548 B2
(45) Date of Patent: Nov. 7, 2023

(54) PHOTODYNAMIC THERAPY APPARATUS FOR LOCAL TARGETING IN CANCER TREATMENT AND CONTROL METHOD THEREFOR

(71) Applicant: AMOS PHARM CO., LTD., Daejeon (KR)

(72) Inventors: Seung Hee Han, Toronto (CA); Brian Wilson, Toronto (CA); Jae Hyuk Kim, Seoul (KR); Sung Ho Lee, Daejeon (KR)

(73) Assignee: AMOS PHARM CO., LTD., Daejeon (KR)

( * ) Notice: Subject to any disclaimer, the term of this patent is extended or adjusted under 35 U.S.C. 154(b) by 263 days.

(21) Appl. No.: 17/258,677

(22) PCT Filed: Jun. 30, 2020

(86) PCT No.: PCT/KR2020/008534
§ 371 (c)(1),
(2) Date: Jan. 7, 2021

(87) PCT Pub. No.: WO2021/261641
PCT Pub. Date: Dec. 30, 2021

(65) Prior Publication Data
US 2022/0134125 A1 May 5, 2022

(30) Foreign Application Priority Data
Jun. 23, 2020 (KR) .................. 10-2020-0076410

(51) Int. Cl.
*A61N 5/06* (2006.01)
*A61N 5/067* (2006.01)

(52) U.S. Cl.
CPC ........... *A61N 5/062* (2013.01); *A61N 5/0603* (2013.01); *A61N 5/067* (2021.08);
(Continued)

(58) Field of Classification Search
CPC ...... A61N 5/062; A61N 5/0603; A61N 5/067; A61N 2005/0611; A61N 2005/0626;
(Continued)

(56) References Cited

U.S. PATENT DOCUMENTS 9,877,784 B2    1/2018  Jung et al.
2005/0113641 A1* 5/2005  Bala ..................... A61B 1/0646
                                          600/104

(Continued)

FOREIGN PATENT DOCUMENTS

JP    H07-136182 A    5/1995
JP    H08-103508 A    4/1996
(Continued)

*Primary Examiner* — Joseph M Dietrich
*Assistant Examiner* — Michael T. Holtzclaw
(74) *Attorney, Agent, or Firm* — ROTHWELL, FIGG, ERNST & MANBECK, P.C.

(57) ABSTRACT

A photodynamic therapy apparatus for local targeting in cancer treatment capable of treating various types of cancers or tumors. An endoscope is placed in the center of an end portion of a probe used in photodynamic therapy and a plurality of optical fibers are arranged along the edge thereof, so that a lesion site is irradiated with a plurality of lights while the plurality of optical fibers of the probe receive lights from individual light sources, respectively, to perform light irradiation individually. An apparatus is disclosed, wherein unnecessary damage to normal tissues is minimized by controlling light irradiation regions, for instance, by defining light irradiation regions encompassing a lesion site from an image provided in real time through an endoscope disposed at an end portion of a probe and allowing only individual light sources irradiating the defined light irradiation regions to emit lights to achieve local light irradiation.

17 Claims, 10 Drawing Sheets

(52) U.S. Cl.
CPC . *A61N 2005/063* (2013.01); *A61N 2005/0611* (2013.01); *A61N 2005/0626* (2013.01); *A61N 2005/0651* (2013.01); *A61N 2005/0665* (2013.01)

(58) Field of Classification Search
CPC ...... A61N 2005/063; A61N 2005/0651; A61N 2005/0665
See application file for complete search history.

(56) References Cited

U.S. PATENT DOCUMENTS

| | | | | |
|---|---|---|---|---|
| 2008/0226029 | A1* | 9/2008 | Weir | A61B 1/07 378/65 |
| 2009/0177094 | A1* | 7/2009 | Brown | A61B 5/0066 606/2 |
| 2010/0145416 | A1* | 6/2010 | Kang | G01J 3/4406 607/90 |
| 2011/0118547 | A1* | 5/2011 | Erikawa | A61B 1/00188 600/108 |
| 2011/0270092 | A1* | 11/2011 | Kang | G01J 3/4406 600/476 |
| 2018/0218508 | A1 | 8/2018 | Lee et al. | |
| 2018/0368915 | A1 | 12/2018 | Xia et al. | |
| 2019/0275346 | A1* | 9/2019 | Maeda | A61B 1/31 |

FOREIGN PATENT DOCUMENTS

| | | | |
|---|---|---|---|
| JP | 2016021978 A | * | 2/2016 |
| KR | 2002-0060020 A1 | | 7/2002 |
| KR | 10-1500620 B1 | | 3/2015 |
| KR | 10-2015-0114376 A | | 10/2015 |
| KR | 10-1670401 B1 | | 10/2016 |
| KR | 10-1784063 B1 | | 10/2017 |
| KR | 10-2018-0095881 A | | 8/2018 |
| WO | 2009-095912 A1 | | 8/2009 |
| WO | 2002-054968 A1 | | 7/2020 |

* cited by examiner

PHOTODYNAMIC THERAPY APPARATUS FOR LOCAL TARGETING IN CANCER TREATMENT AND CONTROL METHOD THEREFOR

CROSS REFERENCE TO RELATED APPLICATION(S)

This application is a 35 U.S.C. 371 National Phase Entry Application from PCT/KR2020/008534, filed on Jun. 30, 2020, designating the United States, which claims the benefit of Korean Patent Application No. 10-2020-0076410, filed on Jun. 23, 2020, respectively, the disclosures of which are incorporated herein in their entireties by reference.

TECHNICAL FIELD

The present invention relates to a photodynamic therapy apparatus for local targeting in cancer treatment and a control method therefor. More specifically, an endoscope is placed in the center of an end portion of a probe used in photodynamic therapy and a plurality of optical fibers are arranged along the edge thereof, so that a lesion site is irradiated with a plurality of lights while the plurality of optical fibers of the probe receive lights from individual light sources, respectively, to perform light irradiation individually. Furthermore, the present invention relates to an apparatus and a control method therefor, wherein unnecessary damage to normal tissues is minimized by controlling light irradiation regions, for instance, by defining light irradiation regions encompassing a lesion site from an image provided in real time through an endoscope disposed at an end portion of a probe and allowing only individual light sources irradiating the defined light irradiation regions to emit lights to achieve local light irradiation. Therefore, the photodynamic therapy apparatus for local targeting and the control method therefor of the present invention are capable of treating various types of cancers or tumors to which local treatment is applicable due to small-sized lesion sites, including cervical cancer, female cancers (endometrial cancer, ovarian cancer, and breast cancer), skin cancer, brain cancer, and the like.

BACKGROUND ART

Cervical cancer is the fourth most common female cancer in the world. According to cancer statistics 2012 from the World Health Organization, there were 500,000 or more cases diagnosed with cancer and approximately 50% of the cases were dead.

Considering the facts that cervical cancer can be completely cured if detected early since the cervical cancer goes through stages of precancerous lesions for a longer period of time compared with other cancers and that the presence or absence of cancer can be determined through simple tests compared with diagnostic examinations of stomach, lung, colon, thyroid cancers, early detection and aggressive treatment for cervical precancerous lesions is important.

There are currently no therapeutic drugs for these cervical precancerous lesions, and the only treatment is surgical excision, and examples of the surgical excision are a loop electrosurgical excision procedure (LEEP), cervical conization, laser excision, and hysterectomy.

However, such surgical therapies cause premature birth, miscarriage, infertility, and the resulting social problems, such as a reduction in fertility rate, and incomplete surgery has a problem regarding a risk of recurrence. Although not high probability, cervical precancerous lesions cause a risk of birth with cerebral palsy caused by premature birth, retinopathy, and decreased lung maturity.

As such, cervical precancerous lesions may increase rapidly among young people and cause serious pregnancy-related complications in existing conization, and thus considering current social circumstances of low fertility, the development of new safe and effective treatments is urgent.

There has recently been newly proposed photodynamic therapy (PDT) in which surgery is performed using a laser, wherein treatment is achieved by selective response to only necessary sites to destroy lesions encompassing cancer cells or precancerous lesions. That is, photodynamic therapy is receiving attention as a treatment method wherein singlet oxygen or free radicals, which are derived by the overall chemical reaction of abundant oxygen in the body, a light (laser) supplied from the outside, and a photo-sensitizer as a material sensitive to a light, treat inflammations of various lesion sites or destroy cancer cells, and thus photodynamic therapy is on the rise as a treatment method capable of pregnancy-related problems due to conventional wide excision.

International Publication No. WO 2009/095912 A1 (published 6 Aug. 2009) discloses, as photodynamic therapy, a method in which a photosensitizer is selectively accumulated only in cancer cells and tumors by conventional injection through an endoscopic catheter and the cervical lesion sites are destroyed by light irradiation.

Korean Patent Publication No. 2002-0060020 (published 16 Jul. 2002) discloses a method for photodynamic therapy and diagnosis, in which two or more laser diodes are provided as a light source. Also in the present case, the lights output from a plurality of laser diodes are collected and condensed to one, and then allowed to exit to a target tissue through an optical cable, thereby achieving treatment.

In most of the PDT apparatuses including ones disclosed in the prior art documents, the lights from a plurality of light sources are condensed to one and allowed to perform light irradiation through one exit, or the lights from a plurality of light sources are directly irradiated at the same time.

Such a light irradiation manner in which the condensed lights are allowed to exit through one exit can increase treatment effects by increasing light intensity, but may cause a problem of skin damage due to the irradiation to tissues in the vicinity of lesion sites. In addition, a manner in which a transferred light is divided into a plurality of lights and irradiated (Korean Patent Registration No. 10-1500620) or a manner in which a plurality of light irradiation parts are allowed to protrude from an endoscope and a plurality of light sources are installed in the protruding light irradiation surfaces, thereby achieving individual light irradiation from each light source (Korean Patent Registration No. 10-1670401) may be applied, but these manners result in light irradiation to a wide area encompassing lesion sites.

Therefore, there has been a need for an apparatus capable of achieving local treatment by intensive light irradiation to only a lesion site while minimizing the damage to adjacent normal tissues when a tumor is located locally in the epithelium of the cervix, like in the treatment of early cervical cancer.

DETAILED DESCRIPTION OF THE INVENTION

Technical Problem

Therefore, the present invention has been made in view of the above-mentioned problems, and an aspect of the present invention is to provide a photodynamic therapy apparatus for local targeting in cancer treatment, wherein in the photodynamic therapy apparatus capable of local treatment, light irradiation regions encompassing a lesion site are selected from an image provided in real time through an endoscope and only the selected light irradiation regions are irradiated with lights, so that damage to normal tissues adjacent to the lesion site can be minimized.

Technical Solution

In accordance with an aspect of the present invention, there is provided a photodynamic therapy apparatus for local targeting in cancer treatment, the apparatus including: a light supply device including: a light source body; a light condenser installed to correspond to the light source body to condense a light irradiated from the light source body; and an optical fiber connected to the light condenser to receive the condensed light through one end thereof and allow the condensed light to exit through the other end thereof; an optical cable configured to extend the optical fiber to the outside of the light supply device; a probe connected to the optical cable to allow the condensed light to exit and receive an internal image of the human body; an image supply device including an image sensor configured to receive the image input from the probe to convert the input image to image data; a monitor configured to receive the converted image data from the image supply device to display the image data; an input device configured to receive selection information; and a controller configured to process the image data from the image supply device to allow an input value of the input device to be contained in the image data and configured to control the light supply device and regulate signal transmission and power supply for the constituent elements of the apparatus.

Furthermore, the light supply device may include: a light source body having a plurality of individual light sources, of which the light on and off and the light intensity are individually controllable; a plurality of light condensers installed to correspond to the plurality of individual light sources of the light source body to condense lights irradiated from the individual light sources, respectively; and optical fibers individually connected to the plurality of light condensers to receive the condensed lights through one ends thereof and allow the condensed lights to exit through the other ends thereof, and the optical cable may bundle the plurality of optical fibers into one bundle and extend the bundled optical fibers to the outside of the light supply device. The probe may include: a body connected to the optical cable to be fixed by an external device or an operator; an insertion tube protruding from the front end of the body to have a rod shape to be inserted into the human body, and having a light exit surface at the end, through which the condensed lights through the plurality of optical fibers exit individually; and a lens installed in the light exit surface of the insertion tube to receive an image at the front.

Furthermore, another form of the light supply device may include: a light source body, of which the light on and off and the light intensity are controllable; one or a plurality of light condensers installed to correspond to the light source body to condense lights irradiated from the light source body, respectively; an entrance light optical fiber individually connected to each of the light condensers to receive the condensed light through one end thereof and allow the condensed light to exit through the other end thereof; a light switch configured to receive the light from the entrance light optical fiber to divide the light into a plurality of lights and allow the divided lights to exit, the divided lights being individually regulated by the light switch; and a plurality of exit light optical fibers configured to receive the lights exiting from the light switch through one ends thereof to allow the lights to exit through the other ends thereof, and the optical cable may bundle the plurality of optical fibers into one bundle and extend the bundled optical fibers to the outside of the light supply device.

Furthermore, in the light source body of the light supply device, the plurality of individual light sources may be installed at equal intervals in a support while the individual light sources are arranged in a lattice arrangement, an arrangement of triangles, or a concentric arrangement in which a plurality of circles are arranged concentrically.

Furthermore, the individual light sources may have any one or two types selected from a laser diode (LD), an injection laser diode (ILD), and a light-emitting diode (LED).

Furthermore, the light condenser of the light supply device may be configured such that an inside surface is formed to be a reflection surface to condense a light to an end of the optical fiber or a condensing lens is used to condense a light to an end of the optical fiber.

Furthermore, the lens of the probe may be an endoscope.

Furthermore, the cancer may be a target of treatment and may be a cancer or tumor to which local treatment is applicable due to a small-sized lesion site.

Then, the controller may include: an image data module configured to receive an image in a lighting state to allow the image sensor to convert the image to image data; an interest area selection module configured to output the image data, converted from the image in the lighting state, to a monitor, allow the input device to select an interest area that is suspected, and apply the interest area to the image data; a target area setting module configured to set the interest area as a target area to be irradiated with light; a light irradiation region setting module configured to check light irradiation regions of the individual light sources through the light exit surface of the probe; and a local light irradiation module configured to select individual light sources, which are to irradiate the set target area with light, and supply power to the selected individual light sources to emit lights.

Furthermore, the image data module may further perform a process of receiving a fluorescent image in a dark state to allow the image sensor to convert the fluorescent image to image data; a fluorescent area setting module may automatically set a fluorescent area 94 with predetermined brightness or higher from the image data converted from the image in the dark state; and the target area setting module may overlap images, to which the interest area and the fluorescent area are applied, to set an overlapping area as a target area.

Furthermore, the local light irradiation module may set individual light sources, which are to be supplied with power, based on whether the center of a light irradiation region of an individual light source is included in the target area.

Furthermore, the local light irradiation module may calculate the minimization of the area of light irradiation regions encompassing the entire target area and then set individual light sources, which are to be supplied with power, based on whether light irradiation regions having a calculated area are irradiated with lights of the individual light sources.

Furthermore, the controller may further include a light output control module configured to control the output intensity of each of individual light sources, of which the turning on and off is determined.

Furthermore, by, among the selected individuals, setting the output intensity of an individual light source to be increased when a light irradiation region of the individual light source is included in the target area by 50-100% and setting the output intensity of an individual light source to be reduced when a light irradiation region of the individual light source is included in the target area by 50% or less, the light output control module may differently apply the light output intensity according to the degree to which a light irradiation region of an individual light source overlaps the target area.

Advantageous Effects

In the photodynamic therapy apparatus for local targeting in cancer treatment of the present invention, an image is acquired through the endoscope installed in the probe, light irradiation regions encompassing a lesion site are selected from the acquired image, and only the selected regions are irradiated with lights, thereby achieving photodynamic therapy while minimizing damage to normal tissues.

In particular, to achieve local light irradiation, a plurality of optical fibers are disposed in the probe, the respective optical fibers that are disposed are respectively provided with the individual light sources, which can be individually regulated, to perform light irradiation, while individual light sources irradiating normal tissues except for a selected area are turned off, thereby reducing the light irradiation regions.

Accordingly, there can be provided an apparatus capable of achieving customized local treatment on various types of cancers and tumors to which local treatment is applicable due to small-sized lesion sites, including not only early cervical cancer but also representative female cancers (endometrial cancer, ovarian cancer, and breast cancer), skin cancer, brain cancer, and the like.

MODE FOR CARRYING OUT THE INVENTION

Figure 1:
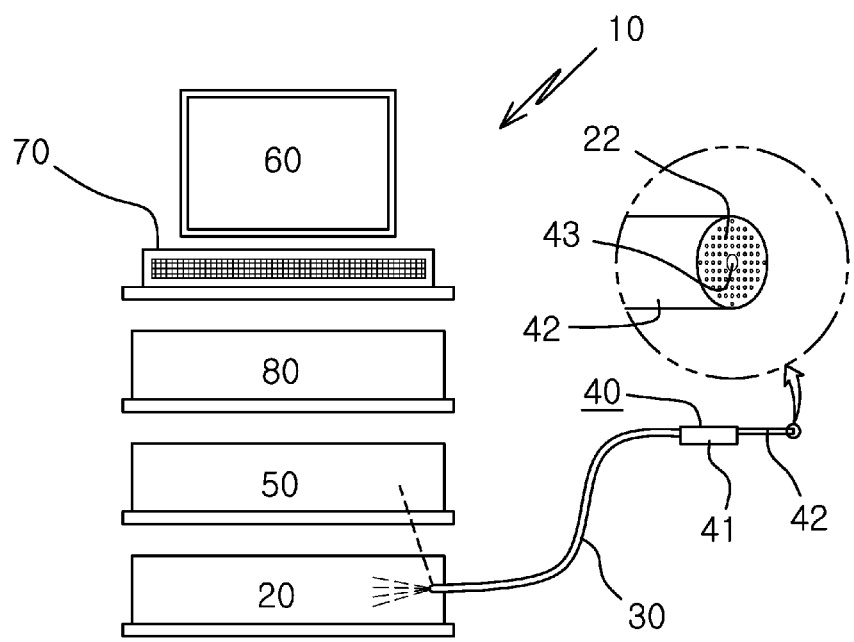
FIG. 1 is a schematic diagram showing a photodynamic therapy apparatus for local targeting according to a preferable embodiment of the present invention.

Hereinafter, embodiments of the present invention will be described in more detail with reference to the accompanying drawings. While the present invention can be variously modified and have alternative forms, specific embodiments have been shown by way of example in the drawings and will be described in detail herein. However, it is to be understood that the present invention is not intended to be limited to the particular forms disclosed. Rather, the intention is to cover all modifications, equivalents, and alternatives falling within the spirit and scope of the invention as defined by the claims. In describing each drawing, like reference numerals are used for like elements. In the accompanying drawings, the dimensions of the structures are shown enlarged or reduced in order to clarify the present invention.

The terms used herein are simply used to describe particular embodiments and are not intended to limit the present invention. A singular expression includes a plural expression unless clearly construed in a different way in the context. It should be understood that the terms, such as "includes", "comprises", or "has" are used to specify the presence of features, numbers, steps, operations, elements, or combinations thereof described in the specification, rather than excluding the possibility of presence or addition of one or more other features, numbers, steps, operations, elements, or combinations thereof in advance.

Unless otherwise defined, all the terms used herein, including technical or scientific terms, have the same meaning as commonly understood by a person having an ordinary skill in the art to which the present invention belongs. Terms as defined in dictionaries generally used should be construed as including meanings which accord with the contextual meanings of related technology, and unless clearly defined herein, the terms should not be construed as having ideal or excessively formal meanings.

FIG. 1 is a diagram showing a photodynamic therapy apparatus for local targeting according to a preferable embodiment of the present invention.

As referenced, a photodynamic therapy apparatus 10 for local targeting according to the present invention includes: a light supply device 20, an optical cable 30 configured to transfer emitted light; a probe 40 configured to irradiate the transferred light and receive an image at the front; an image supply device 50 configured to convert the image received from the probe to image data; a monitor 60 configured to display the converted image data; an input device 70 configured to receive selection information, and a controller 80 configured to regulate various signals.

The photodynamic therapy apparatus 10 for local targeting may be provided in the form in which the respective elements are separated as shown but connected to each other by connection jacks or some elements are integrally coupled, and the photodynamic therapy apparatus 10 may be mounted on a mobile table to thereby facilitate movement.

Figure 2:
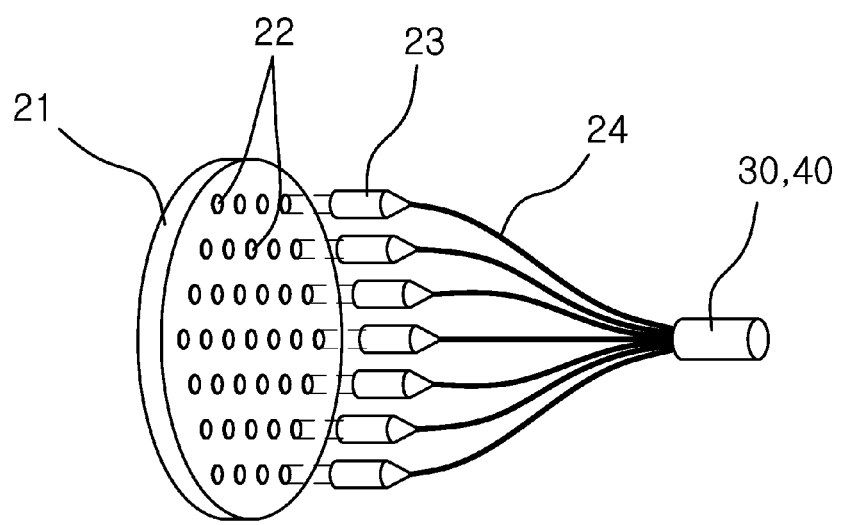
FIG. 2 is a schematic view showing a light supply device according to an embodiment of the present invention.

Referring to FIG. 2, the light supply device 20 includes: a light source body 21 in which a plurality of individual light sources 22 are arranged; light condensers 23 configured to receive and condense lights irradiated from the light source body; and optical fibers 24 configured to transfer the lights condensed in the light condensers. These elements are connected to a cable 30 or a probe 40.

First, the light source body 21 is a device in which the plurality of individual light sources 22 are mounted on a substrate to supply lights by individual regulation. The light source body may be provided in the form in which a plurality of individual light sources are mounted on a single substrate or in the form in which two or more substrates each having a plurality of individual light sources are assembled.

Figure 3A:
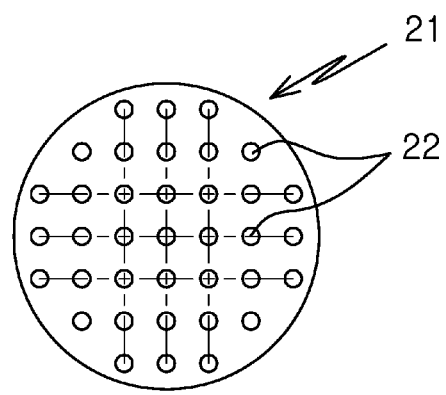
FIGS. 3A to 3C are plane views showing light source bodies having various individual light source arrangement forms according to the present invention.
Figure 3B:
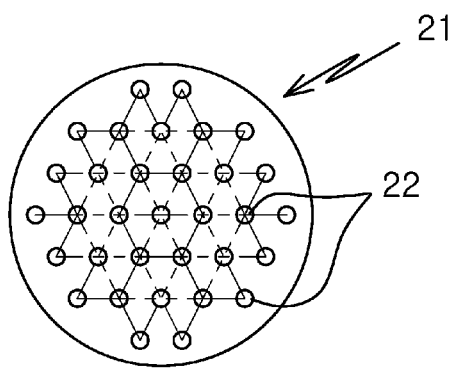
Figure 3C:
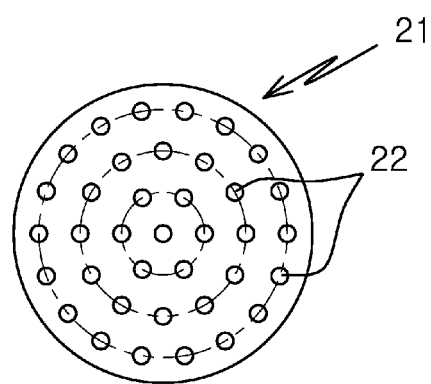

The light source body 21 is formed by a plurality of individual light sources arranged at predetermined intervals in a substrate. The individual light sources 22 may be arranged in a lattice form on a circular substrate to perform light irradiation as shown in FIG. 3A, may be arranged in the form of consecutive triangles to perform light irradiation as shown in FIG. 3B, or may be arranged in a concentric form in which a plurality of circles having different diameters are arranged concentrically, to perform light irradiation as shown in FIG. 3C.

The number of the individual light sources 22 corresponds to the number of optical fibers exposed to a light exit surface at an end of the probe. When the number of optical fibers 24 that are disposed is increased by enlargement of the area of the light exit surface 421, the individual light sources 22 corresponding thereto can be increasingly disposed to perform individual light irradiation.

The individual light sources 22 may have any one type or a mixture of two or more types of a laser diode (LD), an injection laser diode (ILD), and a light-emitting diode (LED).

In addition, the individual light sources 22 each are connected so as to receive power independently, and a regulation unit controlled by the controller 80 is installed on each power supply line, so that the turning on and off of the individual light sources can be independently regulated and the intensities of the individual light sources can be individually controlled by the controller.

Among the plurality of individual light sources 22 arranged, any one may irradiate a visible light to acquire an internal image of the human body, and another may irradiate the light to be diffused, thereby checking the location where a photosensitizer is concentrated in the inside of the human body. The output of the light may be lowered to minimize the irritation to the skin and facilitate fluorescence visualization of the corresponding skin. Individual light sources offering such functionality may be disposed in the center of the light source body or may be deflected to one side, thereby providing such functionality.

Among the individual light sources with functionality, individual light sources irradiating visible light may be used as light sources for an endoscope. That is, while a light is received from the light source body, an internal image of the human body may be separately transferred to the image supply device. In addition, an endoscope line is separately prepared, so that a light source irradiating visible light may be provided from the endoscope line itself but not from the light source body.

In addition, the plurality of light condensers 23 are installed adjacent to the light source body 21. The light condenser 23 receives a large area of light irradiated from the individual light source 22 and condenses the light to one point to allow the light to exit. A single light condenser 23 is installed to correspond to a single individual light source 22 as a set, so individual light irradiation can be achieved through the optical fibers 24 on a light exit surface 421 of the probe 40.

Figure 4A:
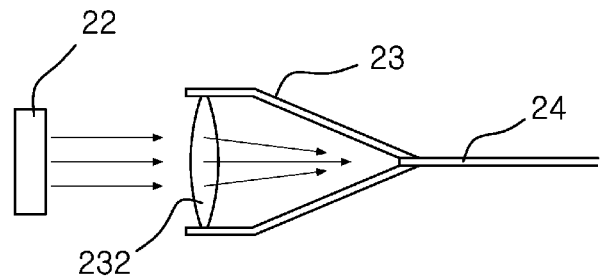
FIGS. 4A and 4B are operational views showing operations of light condensers according to embodiments of the present invention.

The light condenser 23 may be differently provided in a light condensing manner by a condensing lens 232 and in a light condensing manner by a light reflection surface 231. FIG. 4A is a schematic diagram depicting a light condensing form by a condensing lens 232. As shown in FIG. 4A, a condensing lens 232 is formed toward an individual light source 22, so that a light horizontally entering from the individual light source is condensed to one point by the refraction through the condensing lens 232, and an end of the optical fiber 24 is disposed at the point to which the light is condensed, so that a wide area of light from the individual light source is condensed in a point form, inserted into the end surface of the optical fiber, and moved along the optical fiber.

Figure 4B:
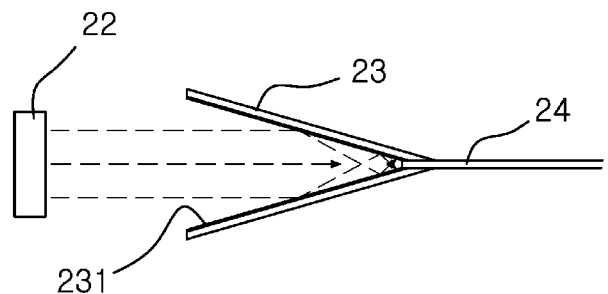

Alternatively, in FIG. 4B, an inside surface of a light condenser 23 has a gradually reduced diameter and formed to be a reflection surface 231, so that a light horizontally entering from an individual light source 22 is refracted to the center along the reflection surface 231 on the inside of the light condenser 23 and thus condensed to one point, and the light condensed to one point is inserted into one end of the optical fiber 24 and moved along the optical fiber.

Therefore, the light condenser 23 is provided in the form in which one end is disposed adjacent to the individual light source 22 and the other end is coupled with the end of the optical fiber 24, so that a wide area of light exiting from the individual light source 22 can be condensed to one point and transferred to the optical fiber 24. The individual light sources are individually regulated, so that the lights irradiated from the probe to a skin site are controlled by the optical fiber unit, thereby minimizing the light irradiation area to normal tissues.

Last, the rear end of the optical fiber 24 is coupled with the front end of the light condenser 23, so that the optical fiber 24 receives the condensed light and allows the condensed light to exit forward through the front end thereof.

As mentioned above, the light supply device 20 including the light source body 21, the light condensers 23, and the optical fibers 24 is extended to the outside by the optical cable 30.

The optical cable 30 bundles the plurality of optical fibers connected to the light condensers into one bundle and extends the bundled optical fibers to the outside of the light supply device. The plurality of optical fibers are bundled inside the light supply device 20, and exposed and extended by the optical cable 30 outside the light supply device.

This optical cable may be partially diverged or may be joined with another cable at one portion, as necessary, thereby transmitting various types of signals or image data, and may be extended by additional installation of an extension cable through a connector.

The cable that is joined or diverged may be a cable connected to the image supply device, and a representative example of the cable may be an endoscope.

In another embodiment of the light supply device of the present invention, a light switch is installed on the optical fiber transferring the light condensed by the light condenser, thereby dividing one entrance light into a plurality of exit lights.

Figure 4C:
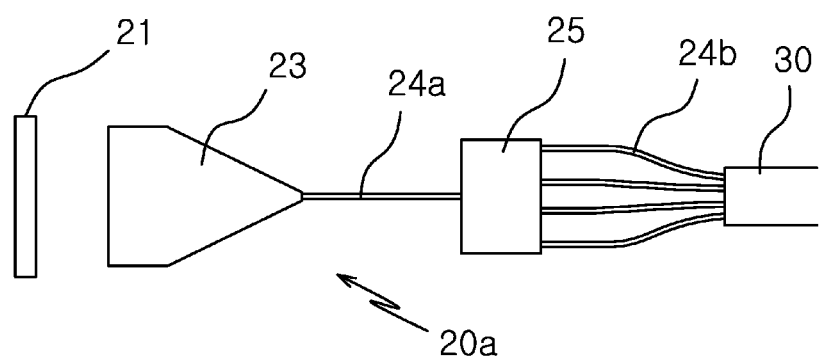
FIGS. 4C to 4E are plane views showing light supply devices according to other embodiments of the present invention.

As shown in FIG. 4C, a light supply device 20a according to another embodiment of the present invention includes: a light source body 21, of which the light on and off and the light intensity are controllable; a light condenser 23 installed to correspond to the light source body to condense a light irradiated from the light source body; an entrance light optical fiber 24a connected to the light condenser to receive the condensed light and allow the condensed light to exit to the other end; a light switch 25 configured to receive the light from the entrance light optical fiber to divide the light into a plurality of lights and allow the divided lights to exit, the divided lights being individually regulated by the light switch; and a plurality of exit light optical fibers 24b configured to receive the lights exiting from the light switch to allow the lights to exit to the other ends. The plurality of exit light optical fibers are bundled into one bundle to be made into an optical cable, which is then extended to the outside and connected to the probe.

Since the light switch can perform the same role as an individual light source in the previous embodiment, the light switch is allowed to regulate any one of the divided lights, thereby producing the same effect as regulating individual light emission of the individual light sources. In addition, the number of lights divided by the light switch may be varied as needed, besides four divided lights as shown in the drawing.

Figure 4D:
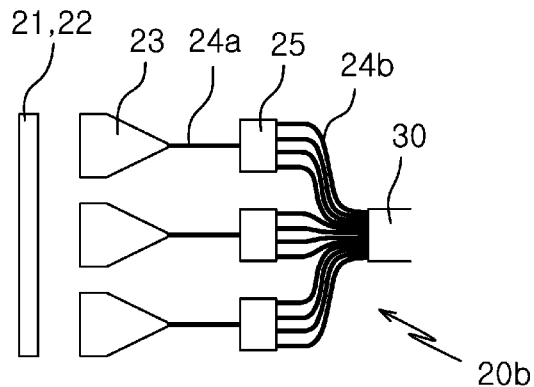

In addition, as shown in FIG. 4D, the light supply device 20b may be provided such that a plurality of light condensers 23 are disposed for a light source body 21 formed of one light source, and light switches 25 are installed on optical fibers 24a connected to the light condensers, respectively, so that the division of light is achieved through a plurality of optical fibers 24b.

Figure 4E:
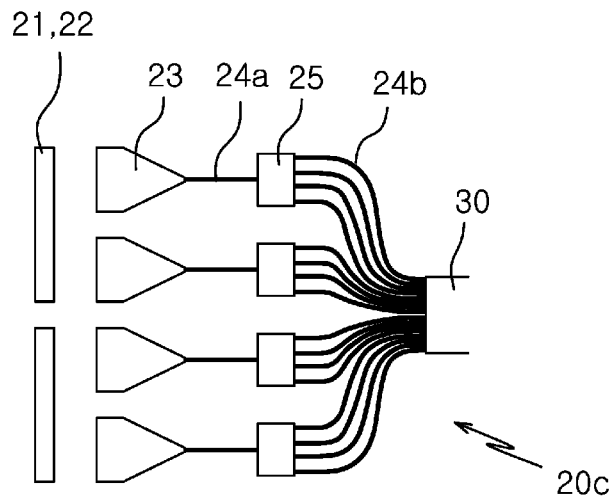

As shown in FIG. 4E, in a light supply device 20c, a plurality of individual light sources 22 are provided as a light source body 21, and a plurality of light condensers 23 are disposed for the individual light sources, respectively, and optical fibers 24a connected to the respective light condensers are connected to light switches 25, and the lights divided by each of the light switches may be transferred through a plurality of optical fibers 24b.

Hereinafter, embodiments of the present invention will be described by an example in which optical fibers are separately regulated through the individual regulation of individual light sources, but a form in which light switches are mounted on optical fibers to provide a function of regulating individual light sources is included within the right scope of the present invention.

The optical cable may be divided into the rear end at the light entrance side and the front end at the light exit side, and the probe 40 is installed on the front end at the light exit side. The probe 40 includes: a body 41; an insertion tube 42 protruding from the front end of the body to be inserted into the human body; and a lens 43 installed in the front end of the insertion tube to receive an internal image of the human body.

The body 41, while containing and fixing the optical cable, may have an expand end surface to thereby provide a portion which a user can grasp, or may be coupled to a separate support or device by forming a fixing unit.

The insertion tube 42 is a portion that protrudes forward from the front end of the body, and the insertion tube is inserted into the human body and disposed adjacent to a skin as a target of testing or treatment. It is therefore preferable that the insertion tube is formed in the form or formed of a material capable of fixing a position, like an endoscope tube body.

A light exit surface 421 is formed on the end of the insertion tube 42. The plurality of optical fibers 24 provided from the optical cable are disposed on the light exit surface 421. The light exit surface 421 may allow lights to exit by direct exposure of the end of the optical cable, or may be provided in the form in which optical fibers are arranged at predetermined intervals by a separate support. The light exit surface may have a structure sealed by a transparent cap in order to prevent the infiltration of foreign materials, and when the light exit surface includes an endoscope, only a portion of the light exit surface, which corresponds to the endoscope, may be partially opened to draw out an endoscope device inside.

When the end of the insertion tube is formed to be a light exit surface having a support, the optical fibers in the light irradiation part of the light exit surface may be arranged in the same forms as the light source bodies in FIGS. 3A and 3B. Also, the individual light sources of the light source body may be arranged in various forms to achieve light condensation by individual regulation, and the optical fibers irradiating the lights through the light exit surface of the insertion tube may be arranged at predetermined intervals inside the circular light exit surface to perform light irradiation according to the shape of a target area, which is an area in need of treatment.

A lens 43 is further installed in the center or at one side of the insertion tube 42 to receive an image, which corresponds to light reflected from the inside of the human body. In addition, a light irradiation part emitting visible light but not treatment wavelengths may be further formed adjacent to the lens to performing light irradiation for providing a reflection light to the lens. The light irradiation part may be provided by any one of the plurality of optical fibers, and an individual light source corresponding to the corresponding optical fiber may be configured to irradiate visible light.

In addition, the lens 43 may be an endoscope. The endoscope may be used in various forms, such as a form of having only a lens, a form of having an outlet at one side, through which a separate surgical instrument can be withdrawn, or a form of configuring a gas outlet together. A driving unit for operating the endoscope may be inserted into a main body of the probe to enable a precise operation of the endoscope.

The optical fibers inside the probe 40 may be wired by direct insertion of the optical cable, or the plurality of optical fibers corresponding to the optical fiber inside the probe are already wired and the optical cable is connected to the rear end of the probe, so that the optical fibers of the optical cable may be correspondingly connected to the optical fibers inside the probe.

Figure 5A:
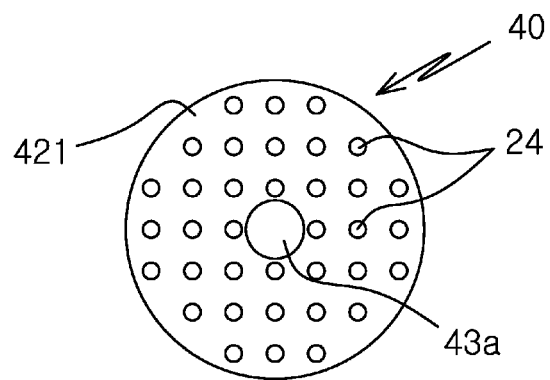
FIGS. 5A and 5B are plane views showing light exit surfaces of probes employing an endoscope as a lens.
Figure 5B:
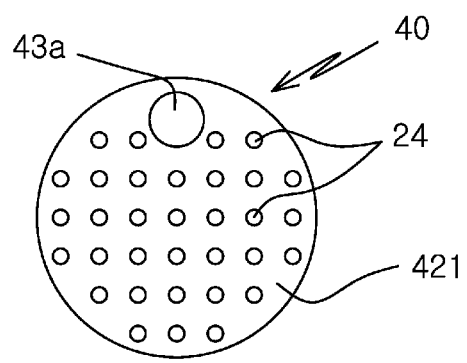

FIGS. 5A and 5B show a light exit surface 421 of a probe employing an endoscope 43a as a lens. As shown in FIG. 5A, the endoscope 43a is placed in the center of the light exit surface of the probe, thereby performing image acquisition. However, the placement of the endoscope in the center keeps the individual optical fibers 24 from being disposed in the endoscope placement region, and thus individual light irradiation may be difficult to control at the center of the light irradiation regions. It is therefore preferable to secure a wide area of light irradiation regions capable of individually controlling light irradiation by placing the endoscope 43a to be deflected to one side on the light exist surface 421 of the probe, as shown in FIG. 5B.

An image inputted to the lens 43 of the probe is transmitted to the image supply device 50 and converted to image data. The image supply device 50 includes an image sensor to convert a reflective-light type of image, inputted from the lens, to image data by using a program.

The image supply device 50 is connected to the monitor 60 to display the converted image data. The monitor usually includes all image output devices capable of outputting images.

An input device 70 is further installed in linkage with the monitor 60. The input device is used as a unit configured to enlarge a portion of an output image or display a portion of the output image. Such an input device commonly includes keyboards and mice, and includes touch screen forms combined with monitors, or communication equipments (smartphones and notebooks) that can be connected by communication.

The controller 80 is configured to process the image data from the image supply device to allow an input value of the input device to be contained in the image data and configured to control the individual light sources of the light supply device and regulate signal transmission and power supply for the constituent elements of the apparatus. Therefore, the controller is connected to all of the light supply device, the probe, the image supply device, the monitor, and the input device, so that the controller analyzes the signals transmitted from each thereof, to thereby perform suitable device operations.

Figure 6A:
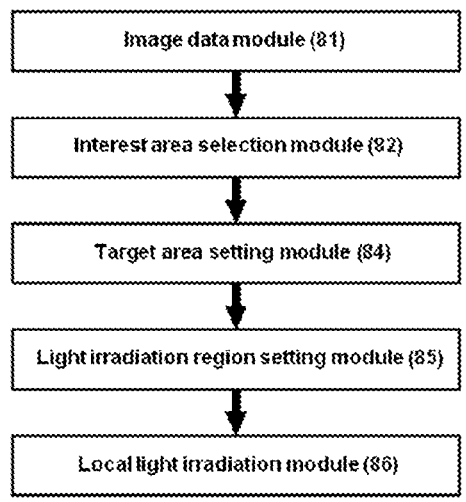
FIGS. 6A and 6B are block diagrams showing a controller according to the present invention.

FIG. 6A is a block diagram showing a representative configuration of the controller.

As referenced, the controller 80 of the present invention includes an image data module 81, an interest area selection module 82, a target area setting module 84, a light irradiation region setting module 85, and a local light irradiation module 86.

A typical configuration in the controller is described on the basis of the execution process with the cervix as a target site to be treated.

First, the image data module 81 performs a process of receiving an image or a fluorescent image in a lighting state and a dark state to allow an image sensor to convert the image to image data.

The image data module 81 inserts a probe into the body such that the probe is inserted into the vicinity of the cervix, which is a site to be treated, supplies power to any one individual light source, preferably an individual light source irradiating visible light, to irradiate a light from a light exit surface at the front end of the probe, allows a lens to receive an internal image obtained by light irradiation and an image sensor to convert the image to generate image data, and transmits and outputs the image data to a monitor.

In addition, a photosensitizer is concentrated in the cancer or tumor after a predetermined time after administration, and thus the photosensitizer can be confirmed in a dark state.

Therefore, the image data module may additionally receive a fluorescent image by creating a dark state after acquiring the internal image by visible light. Also, the image data module may allow the lens to receive the fluorescent image, allow the image sensor to convert the fluorescent image to generate fluorescent image data, and transmit and output the fluorescent image data to the monitor.

The interest area selection module outputs optical image data, acquired by visible light, to the monitor and selects an interest area suspected with cancer or tumor through an input device connected to the monitor.

The interest area selection module may select a partial area on the monitor screen by a signal input through the input device and enlarge and output the selected area. The enlarged and output screen image may be processed and corrected without breaks by a known image editing program.

Figure 7A:
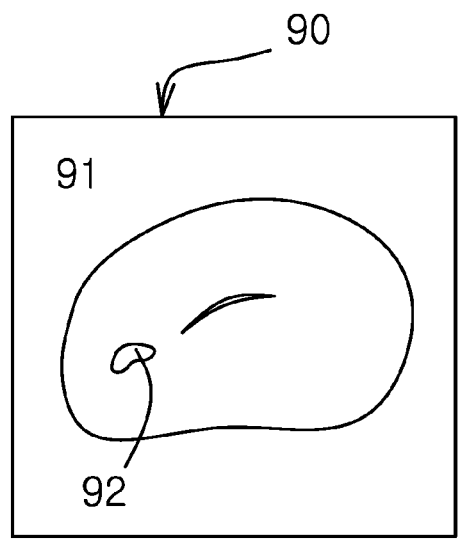
FIGS. 7A and 7B are schematic views showing a lesion site and a selected interest area on a cervical image data screen.
Figure 7B:
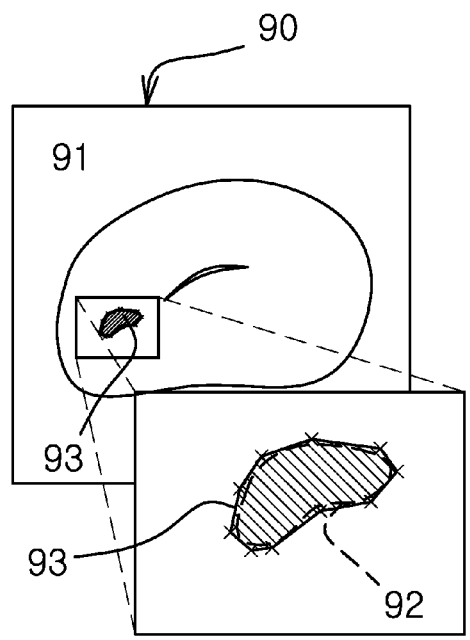

In FIG. 7A, a lesion site 92 can be defined on an image screen 90 of the cervix 91. As shown in FIG. 7B, an operator selects an interest area 93 by using a mouse, a direct touch, or other selection means. Further enlargement of a portion can facilitate selection of the interest area. The selected information is displayed on the monitor and the selected interest area 93 is stored in combination with image data.

Figure 6B:
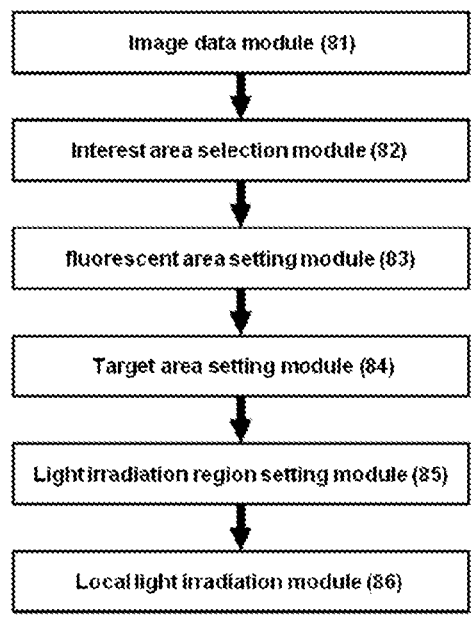

As shown in FIG. 6B, a process by a fluorescent area setting module 83 may be further performed. That is, when a fluorescent image is further received by the image data module 81, the fluorescent area setting module performs a process of automatically setting fluorescent areas, which are parts exhibiting fluorescence, from the fluorescent image data, acquired in a dark state, by using an image editing program.

As an example of fluorescent area selection, a fluorescent area with predetermined brightness or higher may be selected. The fluorescent image data may also be checked by output to the monitor. The brightness setting is gradually changed between low brightness and high brightness through the input device, thereby checking changes of the automatically selected fluorescent areas according to the brightness setting and finally selecting any one of the changed fluorescent areas. When the automatically selected fluorescent area is displayed, the corresponding area is selected as a fluorescent area through the input device using a mouse, a direct touch, or other selection means, and the selected information is displayed on the monitor and the selected fluorescent area is stored in combination with image data.

Figure 8:
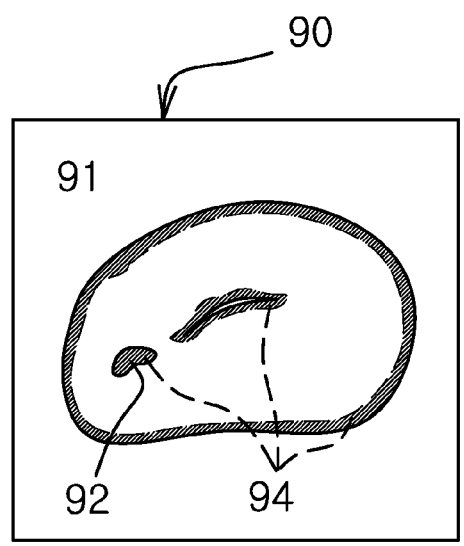
FIG. 8 is a schematic view showing a fluorescent image data screen of the cervix and a selected fluorescent area.

FIG. 8 shows fluorescent image data in a dark state. In most cases, after a predetermined time, a photosensitizer is concentrated only in the lesion site 92 and is removed in most of the other regions. However, in some cases, as shown in the drawing, a small amount of the photosensitizer may remain in areas other than the lesion site. An operator may additionally determine the presence or absence of another lesion site by comparison with the image data obtained using visible light. An error of the fluorescent image data is considered to temporarily appear as if the photosensitizer is concentrated by a lateral surface protruding or depressed in the direction of the lens while a three-dimensional conformation is expressed on a plane. The image data, in which all of the parts exhibiting fluorescence, including the fluorescent site shown due to the error, are selected as a fluorescent area 94, was displayed.

The target area setting module 84 sets the interest area 93 per se as a target area when only the interest area is selected by the interest area selection module.

When the fluorescent area is additionally set by the fluorescent area setting module 83, the target area setting module 84 overlaps two image data, to which the interest area 93 and the fluorescent area 94 are applied, and sets the overlapped area as a target area 95 to be irradiated with light.

Since the images in the lighting state and the dark state are acquired at approximately the same time, the magnification and the location in the cervix can be considered to be almost identical between the two images. However, when the magnifications are different by image enlargement during the selection of the interest area and the fluorescent area, it is preferable that conversion is performed at the same magnification through a previously known graphic program and then a target area is set by overlapping the two image data.

Figure 9A:
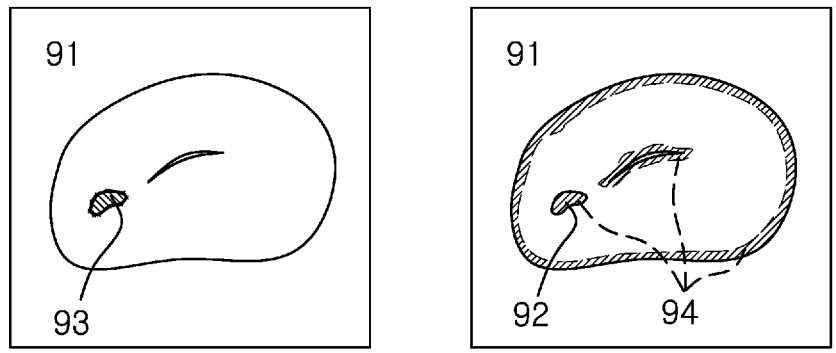
FIGS. 9A and 9B are schematic views showing two image data of an interest area and a fluorescent area, and a target area set by combining the two image data.
Figure 9B:
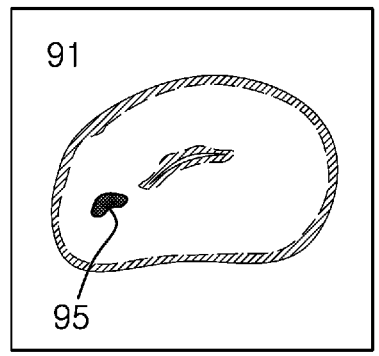

FIG. 9A shows image data with an interested area 93 selected and image data with a fluorescent area 94 set, and FIG. 9B shows an image in which a target area 95 is set by converting two image data at the same magnification and then arranging the two to overlap each other to display an overlapping area of the interest area 93 and the fluorescent area 94.

The light irradiation region setting module 85 performs a process of checking respective light irradiation regions 96 of the individual light sources through the light exit surface of the probe. That is, in the set arrangement structure, the individual light sources are sequentially allowed to emit lights to check which regions of the cervix are irradiated with the lights irradiated from the individual light sources, respectively, and the individual light sources and the light irradiation regions are matched and stored.

The local light irradiation module 86, upon the completion of the setting of the light irradiation regions 96, supplies power to only individual light sources, which perform light irradiation on the set target area 95, to achieve partial light emission, and such partial light emission enables a treatment while the light irradiation to the normal tissues is minimized.

Figure 10A:
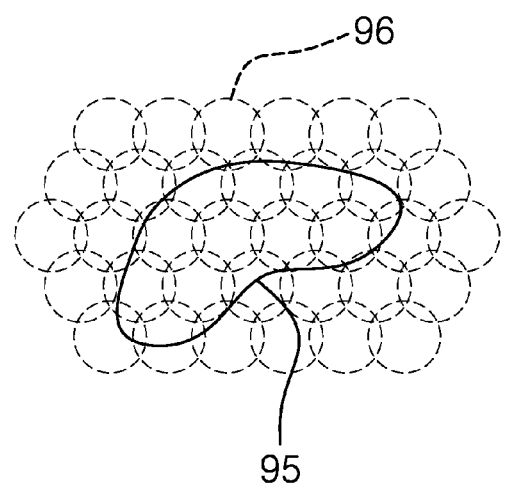
FIG. 10A is a view in which light irradiation regions of respective individual light sources are matched to a target area according to an embodiment of the present invention.
Figure 10B:
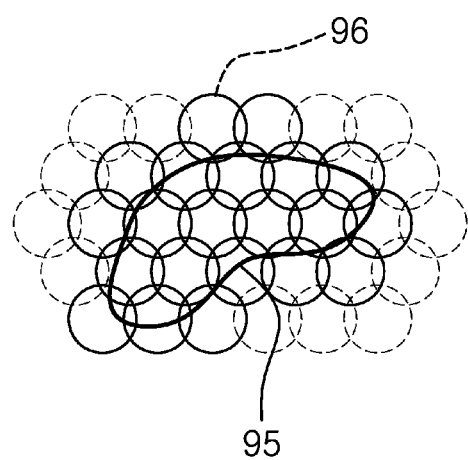
FIG. 10B is an image view in which only individual light sources irradiating a target area are selected to emit lights according to an embodiment of the present invention.

FIG. 10A is a view in which the target area 95 is matched to the light irradiation regions 96 of the individual light sources. In FIG. 10B, only individual light sources corresponding to the light irradiation regions 96 overlapping at least a portion of the target area 95 were supplied with power and operated, and the other individual light sources were turned off, thereby minimizing damage to the normal tissue.

Figure 10C:
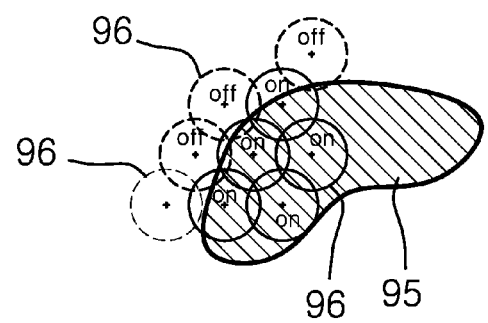
FIG. 10C is a schematic view depicting that selective light emission is performed based on the position of the center of a light irradiation region of an individual light source according to an embodiment of the present invention.

As for a method of controlling the plurality of individual light sources, the individual light sources may be selectively supplied with power based on whether or not the center of a light irradiation region 96 of an individual light source is included in the target area 95. As shown in FIG. 10C, the individual light sources can be allowed to selectively emit lights by a method in which some lights are irradiated to the target area 95 wherein the individual light sources corresponding to the light irradiation regions 96 with centers deviating from the target area are powered off and only the individual light sources with centers included in the target area 95 are powered on. Such a method of determining whether an individual light source is operated according to the center of the light irradiation region should be applied when the light irradiation regions of the individual light sources partially overlap, preferably adjacent light irradiation regions overlap by at least 40% in diameter, and in such cases, the target area can be included in the overall light irradiation regions of the operating individual light sources even on the basis of the centers of the light irradiation regions of the individual light sources.

As for another method of controlling the plurality of individual light sources, the minimization of the area of a plurality of light irradiation regions encompassing the entire target area is calculated by a program and then only individual light sources corresponding to the calculated light irradiation area are selectively supplied with power to emit lights. That is, light irradiation regions of all of individual light sources which irradiate light to at least a portion of the target area are first selected, and among the selected light irradiation regions of the individual light sources, light irradiation regions of individual light sources, which, even though removed, can be compensated for by other light irradiation regions to result in light irradiation to the target area, are second selected and removed, so that the light irradiation regions overlapping the target area are finally selected and only the individual light sources corresponding to the selected light irradiation regions are operated to emit lights.

The local light irradiation module 86 may set the light irradiation regions by moving a probe back and forth according to the size of the target area and then selectively operating the individual light sources, besides a method in which a plurality of individual light sources corresponding to the target area are selected while the probe is fixed. The probe may be moved forward and backward and the target area may be irradiated with a plurality of lights at one time, or the target area may be divided into a plurality of areas and then the probe may be moved to the divided target areas to perform light irradiation.

Figure 11A:
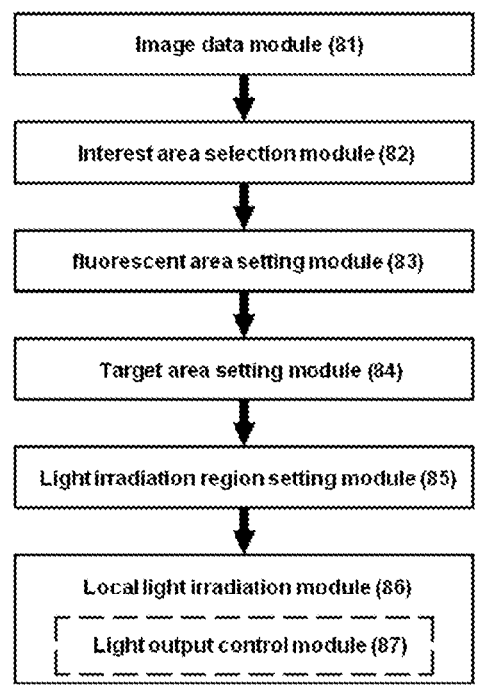
FIG. 11A is a block diagram showing the configuration of a controller including a light output control module according to an embodiment of the present invention.

The controller 80 may further include a light output control module 87 as shown in FIG. 11A. The light output control module 87 may be set as a sub-module subordinating to the local light irradiation module.

The light output control module 87 controls the output intensity of each of the individual light sources, of which the turning on and off is determined, thereby irradiating a normal tissue and a target area-forming tissue with lights of different intensities, so that the normal tissue adjacent to the target area is minimally damaged and the cancer or tumor in the target area are irradiated with lights of strong intensities. The output intensities are set in advance such that light irradiation may be performed by stages according to the set values.

The light output intensity is differentiated according to the degree to which the light irradiation region of the individual light source overlaps the target area. For example, the light irradiation may be performed such that the output intensity of an individual light source is set to be high when a light irradiation region of the corresponding individual light source is included in the target area by 50-100%, and the output intensity of an individual light source is set to be low when a light irradiation region of the corresponding individual light source is contained in the target area by 50% or less.

Figure 11B:
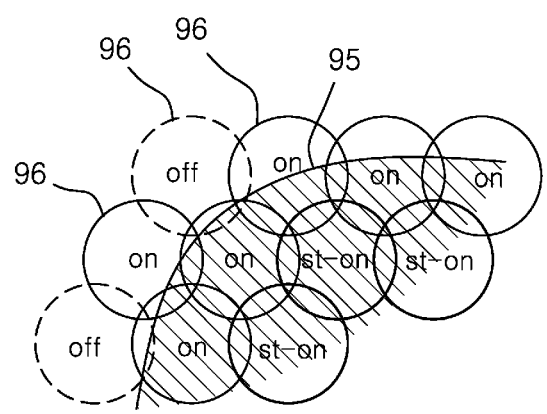
FIG. 11B is a schematic view showing output intensity setting states of individual light sources by the relationship between an individual light source and a target area according to an embodiment of the present invention.

Referring to FIG. 11B, when a light irradiation region 96 (st-on) of an individual light source is entirely included in the target area 95, the output intensity of the corresponding individual light source is increased. When a light irradiation region 96 (off) of an individual light source contains a portion of the target area but can be compensated for by other light irradiation regions, the corresponding individual light source is powered off to remove the light irradiation region. When a light irradiation region 96 (on) of an individual light source contains a portion of the target area but cannot be compensated for by other light irradiation regions, the corresponding individual light source is powered on and the output intensity of the corresponding individual light source is maintained to be medium or low.

The embodiments of the present invention have been described for cervical cancer, but the present invention can be used in photodynamic therapies for various types of cancers and tumors to which local treatment is applicable due to small-sized lesion sites, including other female cancers (endometrial cancer, ovarian cancer, and breast cancer), skin cancer, and brain cancer.

According to a control method for the photodynamic therapy apparatus for local targeting according to the present invention, the target area, which corresponds to a tissue to be treated, is defined and treated by controlling power transmitted to each of the plurality of individual light sources through image analysis of tissue surface.

Specifically, the method may include: an image data step of receiving an image in a lighting state to allow the image sensor to convert to the image to image data; an interest area selection step of outputting the image data, converted from the image in the lighting state, to the monitor, allowing the input device to select a suspected interest area 93, and applying the interest area to the image data; a target area setting step of setting the interest area as a target area 95 to be irradiated with lights; a light irradiation region setting step of checking light irradiation regions 96 of individual light sources through the light exit surface of the probe; and a local light irradiation step of selecting individual light sources, which are to irradiate the set target area with lights, and supplying power to the selected individual light sources to emit lights.

In the image data step, a process of receiving a fluorescent image in a dark state to allow the image sensor to convert the fluorescent image to image data is further performed. In a fluorescent area setting step, a fluorescent area 94 with predetermined brightness or higher is automatically set from the image data converted from the image in the dark state.

In addition, in the target area setting step, images, to which the interest area 93 and the fluorescent area 94 are applied, are allowed to overlap each other to set an overlapping area as a target area 95.

In the local light irradiation step, individual light sources to be supplied with power are set based on whether the center of a light irradiation region 96 of an individual light source is included in the target area 95.

In the local light irradiation step, the minimization of the area of light irradiation regions encompassing the entire target area 95 is calculated and then individual light sources to be supplied with power are set based on whether light irradiation regions having a calculated area are irradiated with lights of the individual light sources.

The method may further include a light output control step of controlling the output intensity of each of individual light sources, of which the turning on and off is determined.

In the light output control step, by, among the selected individuals, setting the output intensity of an individual light source to be increased when a light irradiation region 96 of the individual light source is included in the target area by 50-100% and setting the output intensity of an individual light source to be reduced when a light irradiation region of the individual light source is included in the target area by 50% or less, the light output intensity may be differently applied according to the degree to which a light irradiation region 96 of an individual light source overlaps the target area 95.

The invention claimed is:

1. A photodynamic therapy apparatus for local targeting in cancer treatment, the apparatus comprising:
   a light supply device comprising: a light source body; a light condenser installed to correspond to the light source body to condense a light irradiated from the light source body; and
   an optical fiber connected to the light condenser to receive a condensed light through one end thereof and allow the condensed light to exit through the other end thereof;
   an optical cable configured to extend the optical fiber to the outside of the light supply device;
   a probe connected to the optical cable to allow the condensed light to exit and receive an internal image of a human body;
   an image supply device comprising an image sensor configured to receive the image input from the probe to convert the image input to image data;
   a monitor configured to receive the converted image data from the image supply device to display the image data;
   an input device configured to receive selection information; and
   a controller configured to process the image data from the image supply device to allow an input value of the input device to be contained in the image data and configured to control the light supply device and regulate signal transmission and power supply for the apparatus,
   wherein in the light supply device, the light source body has a plurality of individual light sources, having the light intensity, including whether the light is on or off, being individually controllable; the light condenser has a plurality of light condensers installed to correspond to the plurality of individual light sources of the light source body to condense light irradiated from the individual light sources, respectively; and the optical fiber has a plurality of optical fibers individually connected to the plurality of light condensers to receive a condensed light through one ends thereof and allow the condensed light to exit through the other ends thereof,
   wherein the optical cable bundles the plurality of optical fibers into one bundle and extends the bundled optical fibers to the outside of the light supply device; and
   wherein the controller comprises:
   an image data module configured to receive the image in a lighting state to allow the image sensor to convert the image input into the image data and to receive a fluorescent image in a dark state to allow the image sensor to convert the fluorescent image into the image data;
   an interest area selection module configured to output the image data, converted from the image in the lighting state, to the monitor, and to apply information on the interest area input through the input device to the image data;
   a fluorescent area setting module configured to automatically set a fluorescent area with predetermined brightness or higher from the image data converted from the image in the dark state;
   a target area setting module configured to set an overlapping area in which images to which the interest area and the fluorescent area are applied overlap, as a target area to be irradiated with light;
   a light irradiation region setting module configured to form light irradiation regions in which light exits to a light exit surface of the probe, being formed by partially overlapping respective light irradiation regions of individual light sources and light irradiation regions of other individual light sources adjacent thereto and to check the respective light irradiation regions of the individual light sources by emitting lights from individual light sources sequentially; and
   a local light irradiation module configured to supply power only to individual light sources which irradiate the set target area with lights, among the plurality of individual light sources, to emit light.

2. The photodynamic therapy apparatus for local targeting of claim 1, wherein in the light supply device, the optical fiber has an entrance light optical fiber individually connected to each of the light condensers to receive the condensed light through one end thereof and allow the condensed light to exit through the other end thereof; and the light supply device further comprises a light switch configured to receive the light from the entrance light optical fiber to divide the light into a plurality of lights and allow the divided lights to exit, the divided lights being individually regulated by the light switch; and a plurality of exit light optical fibers configured to receive the lights exiting from the light switch through one ends thereof to allow the lights to exit through the other ends thereof.

3. The photodynamic therapy apparatus for local targeting of claim 1, wherein the light condenser of the light supply device is configured such that an inside surface of the light condenser is formed to be a reflection surface to condense a light to an end of the optical fiber or a condensing lens is used to condense a light to an end of the optical fiber.

4. The photodynamic therapy apparatus for local targeting of claim 1, wherein the photodynamic therapy apparatus is configured to treat a cancer or tumor to which local treatment is applicable due to a small-sized lesion site.

5. The photodynamic therapy apparatus for local targeting of claim 1, wherein in the light source body of the light supply device, the plurality of individual light sources are installed at equal intervals in a support while the individual light sources are arranged in a lattice arrangement, an arrangement of triangles, or a concentric arrangement in which a plurality of circles are arranged concentrically.

6. The photodynamic therapy apparatus for local targeting of claim 5, wherein the individual light sources have any one or two types selected from a laser diode (LD), an injection laser diode (ILD), and a light-emitting diode (LED).

7. The photodynamic therapy apparatus for local targeting of claim 1, wherein the probe comprises: a body connected to the optical cable to be fixed by an external device or an operator; an insertion tube protruding from the front end of the body to have a rod shape to be inserted into the human body, and having a light exit surface at the end, through which the condensed lights through the plurality of optical fibers exit individually; and a lens installed in the light exit surface of the insertion tube to receive the internal image at the light exit surface.

8. The photodynamic therapy apparatus for local targeting of claim 7, wherein the lens of the probe is objective lens of the endoscope.

9. The photodynamic therapy apparatus for local targeting of claim 1, wherein the local light irradiation module sets individual light sources, which are to be supplied with power, based on whether the center of a light irradiation region of an individual light source is included in the target area.

10. The photodynamic therapy apparatus for local targeting of claim 1, wherein the local light irradiation module calculates the minimization of the area of light irradiation regions encompassing the entire target area and then sets individual light sources, which are to be supplied with power, based on whether light irradiation regions having a calculated area are irradiated with lights of the individual light sources.

11. The photodynamic therapy apparatus for local targeting of claim 1, wherein the controller further comprises a light output control module configured to control the output intensity of each of the individual light sources, of which the turning on and off is determined.

12. The photodynamic therapy apparatus for local targeting of claim 11, wherein by, among the selected individuals, setting the output intensity of an individual light source to be increased when a light irradiation region of the individual light source is included in the target area by 50-100% and setting the output intensity of an individual light source to be reduced when a light irradiation region of the individual light source is included in the target area by 50% or less, the light output control module differently applies the light output intensity according to the degree to which a light irradiation region of an individual light source overlaps the target area.

13. A control method for the photodynamic therapy apparatus for local targeting according to claim 1, comprising:
an image data step of receiving an image in a lighting state to allow the image sensor to convert the image into the image data and receiving a fluorescent image in a dark state to allow the image sensor to convert the fluorescent image into the image data;
an interest area selection step of outputting the image data, converted from the image in the lighting state, to the monitor, and applying information on an interest area through an input device to the image data;
a fluorescent area setting step of automatically setting a fluorescent area with predetermined brightness or higher from the image data converted from the image in the dark state;
a target area setting step of setting an overlapping area in which images to which the interest area and the fluorescent area are applied overlap as the target area to be irradiated with lights;
a light irradiation region setting step of forming light irradiation regions in which lights exit to a light exit surface of the probe, by partially overlapping respective light irradiation regions of individual light sources and light irradiation regions of other individual light sources adjacent thereto and checking respective light irradiation regions of individual light sources by emitting lights from individual light sources sequentially; and
a local light irradiation step of supplying power only to individual light sources which irradiate the set target area with light, among the plurality of individual light sources, to emit lights.

14. The method of claim 13, wherein in the local light irradiation step, individual light sources to be supplied with power are set based on whether the center of a light irradiation region of an individual light source is included in the target area.

15. The method of claim 13, wherein in the local light irradiation step, the minimization of the area of light irradiation regions encompassing the entire target area is calculated and then the individual light sources to be supplied with power are set based on whether light irradiation regions having a calculated area are irradiated with lights of the individual light sources.

16. The method of claim 13, further comprising a light output control step of controlling the output intensity of each of the individual light sources, of which the turning on and off is determined.

17. The method of claim 16, wherein in the light output control step, by, among the selected individuals, setting the output intensity of an individual light source to be increased when a light irradiation region of the individual light source is included in the target area by 50-100% and setting the output intensity of an individual light source to be reduced when a light irradiation region of the individual light source is included in the target area by 50% or less, the light output intensity is differently applied according to the degree to which a light irradiation region of an individual light source overlaps the target area.

* * * * *